(12) United States Patent
Multari et al.

(10) Patent No.: US 11,156,556 B1
(45) Date of Patent: Oct. 26, 2021

(54) METHOD AND APPARATUS FOR DETECTING PATHOGENS AND CHEMICALS IN COMPLEX MATRICES USING LIGHT EMISSIONS FROM A LASER SPARK

(71) Applicant: Creative LIBS Solutions LLC, Bernalillo, NM (US)

(72) Inventors: Rosalie A. Multari, Bernalillo, NM (US); David A. Cremers, Bernalillo, NM (US); Ann L. Nelson, Bernalillo, NM (US)

(*) Notice: Subject to any disclaimer, the term of this patent is extended or adjusted under 35 U.S.C. 154(b) by 0 days.

(21) Appl. No.: 16/780,141

(22) Filed: Feb. 3, 2020

Related U.S. Application Data (60) Provisional application No. 62/805,180, filed on Feb. 13, 2019.

(51) Int. Cl.
  *G01N 21/71* (2006.01)
  *G01N 33/49* (2006.01)

(52) U.S. Cl.
  CPC .......... *G01N 21/718* (2013.01); *G01N 33/49* (2013.01); *G01N 2201/129* (2013.01)

(58) Field of Classification Search
  CPC .................................................. G01N 21/718
  USPC ......................................................... 356/39
  See application file for complete search history.

(56) References Cited

U.S. PATENT DOCUMENTS

| | | | |
|---|---|---|---|
| 9,625,376 B2 | 4/2017 | Elsoee | |
| 10,309,880 B2 | 6/2019 | Melikechi | |
| 2009/0290151 A1* | 11/2009 | Agrawal | G01N 21/03 356/318 |
| 2011/0171636 A1 | 7/2011 | Melikechi | |
| 2011/0246145 A1 | 8/2011 | Multari | |
| 2015/0036138 A1* | 2/2015 | Watson | G01N 21/65 356/402 |
| 2015/0284763 A1 | 8/2015 | Rehse | |

(Continued)

OTHER PUBLICATIONS

Cremers, D.A.; Radziemski, L.J. (2013) Handbook of Laser-Induced Breakdown Spectroscopy, 2nd ed., John Wiley, and Sons: Chichester, U.K., pp. 1-27.

(Continued)

*Primary Examiner* — Tarifur R Chowdhury
*Assistant Examiner* — Omar H Nixon
(74) *Attorney, Agent, or Firm* — Wilcox & Myers, P.C.; Jeffrey D. Myers (57) ABSTRACT

An apparatus (and concomitant method) for rapid detection of a plurality of pathogens and/or chemicals, comprising a laser generating laser-induced breakdown spectra from a sample inserted into the apparatus, a receiver recording the spectra, and a data analysis component acquiring the spectra from the receiver and a display and/or data storage component displaying and/or receiving from the data analysis component which pathogens and/or chemicals are present in the sample and/or the likelihood of such presence, wherein the data analysis component comprises: predictive models for the plurality of pathogens and/or chemicals, a queue to order automated analysis by the predictive models in a predetermined order, and statistical analysis models for each of the predictive models to automatically provide likelihoods of presence of the respective pathogens and/or chemicals.

18 Claims, 9 Drawing Sheets

(56) References Cited

U.S. PATENT DOCUMENTS

| | | | | |
|---|---|---|---|---|
| 2016/0018325 | A1* | 1/2016 | Elsoee | G01N 21/35 356/51 |
| 2016/0238522 | A1* | 8/2016 | Lednev | G01N 21/3586 |
| 2017/0261512 | A1* | 9/2017 | Anderson | G01N 33/96 |
| 2018/0360390 | A1* | 12/2018 | Gaudiuso | A61B 5/08 |
| 2018/0375790 | A1* | 12/2018 | Dadashikelayeh | G06F 9/4806 |

OTHER PUBLICATIONS

Diedrich, J.; Rehse, S.J; Palchaudhuri, S. (2007) *Escherichia coli* identification and strain discrimination using nanosecond laser-induced breakdown spectroscopy, Appl. Phys. Lett. 90, 163901 1 3.

Fisher, C.; Multari, R.; Nelson, A.; Cremers, D.A. and Duncan, R. (2017) Multiplex Detection of Protozoan, Bacterial, and Viral Pathogens in Human Blood Using Laser-Induced Breakdown Spectroscopy, 25th International Biodetection Technologies Conference, Jun. 26-28, Alexandria, VA USA.

Fisher, C.; Multari, R.; Cremers, D.A.; Nelson, A.; Young, S.; Karimi, Z. and Duncan, R. (2018) Multiplex Detection of Protozoan, Bacterial, and Viral Pathogens in Human Blood Using Laser-Induced Breakdown Spectroscopy, 26th International Biodetection Technologies Conference, Jun. 27-28, Bethesda, MD USA.

Morel, S.; Leone, N.; Adam, P.; Amouroux, J. (2003) Detection of bacteria by time resolved laser-induced breakdown spectroscopy, Appl. Opt. 42, 6184-6191.

Multari, R.A.; Cremers, D.A.; Dupre, J.M. and Gustafson, J.E. (2010) The Use of Laser-Induced Breakdown Spectroscopy (LIBS) for Distinguishing Between Bacterial Pathogen Species and Strains, Appl. Spectrosc. 64, 750-759.

Multari, R.A.; Cremers, D.A. and Bostian, M.L. (2012) Use of laser-induced breakdown spectroscopy for the differentiation of pathogens, and viruses on substrates, Appl. Opt. 51, B57-B64.

Multari, R.A.; Cremers, D.A.; Scott, T. and Kendrick, P. (2013) Detection of Pesticides and Dioxins in Tissue Fats and Rendering Oils Using Laser-Induced Breakdown Spectroscopy (LIBS). J. Agric Food Chem. 61, 2348-2357.

Multari, R.A.; Cremers, D.A.; Dupre, J.M. and Gustafson, J.E. (2013b) The Detection of Biological Contaminants on Foods and Food Surfaces Using Laser-Induced Breakdown Spectroscopy (LIBS). J. Agric Food Chem. 61, 8687-8694.

Multari, R.A.; Cremers, D.A.; Bostian, M.L.; Dupre, J.M. and Gustafson, J.E. (2013c) Proof of Principle for a Real-Time Pathogen Isolation Media Diagnostic: The Use of Laser-Induced Breakdown Spectroscopy (LIBS) to Discriminate Bacterial Pathogens and Antimicrobial-Resistant *Staphylococcus aureus* Strains Grown on Blood Agar, J. Pathogens 2013, Article ID 898106, 11 pages; http://dx.doi.org/10.1155/2013/898106.

Multari, R.; Cremers, D.A.; Duncan, R. and Young, S. (2013d) Laser-Induced Breakdown Spectroscopy as a Rapid, In-situ Clinical Diagnostic, 21st International Conference on Biodetection Technologies 2013 Technological Advances in Detection & Identification of Biological Threats, Alexandria, Virginia, USA, 18-19.

Multari, R.A., , D.A. Cremers, A. Nelson, Z. Karimi, S. Young, C. Fisher and R. Duncan. (2019) The use of laser-based diagnostics for the rapid identification of infectious agents in human blood. Journal of Applied Microbiology 126, 1606-1617.

Diedrich, J., Rehse, S.J.; and Palchaudhuri, S. (2007) Pathogenic *Escherichia coli* strain discrimination using laser-induced breakdown spectroscopy, J. Appl. Phys. 102, 014702.

Putnam, Russell; Mohaidat, Q.I.; Daabous, Andrew; and Rehse, Steven. (2013) A Comparison of Multivariate Analysis Techniques and Variable Selection Strategies in a Laser-Induced Breakdown Spectroscopy Bacterial Classification. Spectrochimica Acta Part B: Atomic Spectroscopy, 87, 161-167.

Malenfant, Dylan J., Derek J. Gillies, and Steven J. Rehse. (2016) Bacterial Suspensions Deposited on Microbiological Filter Material for Rapid Laser-Induced Breakdown Spectroscopy Identification. Applied Spectroscopy 2016, vol. 70(3) 485-493.

Kochelek, Kristen A, Nancy J. McMillan, Catherine E. McManus and David I. Daniel. (2015) Provenance determination of sapphires and rubies using laser-induced breakdown spectroscopy and multivariate analysis. American Mineralogist, vol. 100, pp. 1921-1931, 2015.

Sivakumar, P., A. Fernandez-Bravo, L. Taleh, J.F. Biddle, and N. Melikechi. (2015) Detection and Classification of Live and Dead *Escherichia coli* by Laser-Induced Breakdown Spectroscopy. Astrobiology vol. 15, No. 2, pp. 144-153, 2015.

\* cited by examiner

Example diagram of a possible detection algorithm flow. Predictive models are created using any combination of spectra collected from pathogens and are arranged in a logical flow to optimize the detection of the presence of the pathogens in the complex matrix. Statistical analysis is applied to the predictions from the models and is included in the decision tree to identify the pathogens present.

- Culture 100 μL of blood before spiking with *S. aureus*
- Control for contamination
- Result: No growth

- Culture 100 μL of blood + *S. aureus* (1000 cells/mL)
- Monitor number of the cells before adding to the filters
- Result: ≈100 colonies which represent a concentration of 1000 cells/mL

- 500 μl blood + *S. aureus* (1000 cells/mL) was deposited on the filter
- Filter heated above 80°C; total heating time 4 min.
- Heated filter cultured for 24 hours to check for growth
- Results: No growth

Analysis Results for Sample # 1963

| | |
|---|---|
| Pathogen A | Detected |
| Pathogen B | Not Detected |
| Pathogen C | Detected |
| Pathogen D | Detected |
| Pathogen E | Not Detected |
| etc. | |
| | |
| Chemical A | Not Detected |
| Chemical B | Not Detected |
| Chemical C | Detected |
| Chemical D | Detected |
| Chemical E | Not Detected |
| etc. | |

FIG 10.

METHOD AND APPARATUS FOR DETECTING PATHOGENS AND CHEMICALS IN COMPLEX MATRICES USING LIGHT EMISSIONS FROM A LASER SPARK

CROSS-REFERENCE TO RELATED APPLICATIONS

This application claims priority to and the benefit of the filing of U.S. Provisional Patent Application Ser. No. 62/805,180, filed on Feb. 13, 2019, and the specification and claims thereof are incorporated herein by reference.

STATEMENT REGARDING FEDERALLY SPONSORED RESEARCH OR DEVELOPMENT

This invention was made with government support under Grant Number 1 R43HL133525-01 awarded by the National Institutes of Health. The government may have certain rights in the invention.

NAMES OF PARTIES TO JOINT RESEARCH AGREEMENT

Not Applicable.

REFERENCE TO A SEQUENCE LISTING, A TABLE, OR A COMPUTER PROGRAM LISTING COMPACT DISC APPENDIX

Not Applicable.

STATEMENT REGARDING PRIOR DISCLOSURES BY THE INVENTOR OR A JOINT INVENTOR

Not Applicable.

BACKGROUND OF THE INVENTION

Field of the Invention (Technical Field)

The present invention relates to the detection of pathogens and/or chemicals, and more particularly, to laser-based analysis methods such as Laser-Induced Breakdown Spectroscopy.

Description of Related Art

Methods of rapidly detecting pathogens and/or chemicals in complex matrices such as blood or other bodily fluids is of great interest for medical applications for either patient treatment/monitoring, or ensuring the safety of the donor blood supply. Today, the detection of an infection and the identification of the responsible organism typically requires up to 72 hours, depending on the pathogen; the use of highly skilled personnel; and complex sample preparation. In addition, transport of a blood sample to a microbiology laboratory for analysis is often required. The ability to rapidly (within minutes) diagnose bloodborne infections on-site, with simple sample preparation and no requirement for highly skilled personnel would greatly enhance the ability to identify, contain, and treat bloodborne infections as well as greatly reduce the time needed to screen donated blood for infections.

Methods for rapidly detecting pathogens and chemicals in complex matrices such as foods, food preparation surfaces, and food preparation bi-products such as rendered oils are important to food safety. For example, bacterial contaminations of *E. coli* O157:H7 have caused moderate to severe illness or death, with most of the deaths occurring in children under 5 years of age or the elderly. The bacteria *S. enterica* is also responsible for severe illness and death in people. Common sources of infection are meat, poultry, eggs, milk, and products of eggs and milk. To ensure food safety, a rapid means of detecting the presence of harmful pathogens and/or chemicals is an important step in enhancing food safety.

Laser-based analysis methods show great promise as a tool for providing rapid, real-time detection of pathogens and/or chemicals in complex matrices. In particular, the use of a laser-spark as is used in Laser-Induced Breakdown Spectroscopy (LIBS) shows great promise as a diagnostic tool and has been investigated by many researchers. LIBS is an established spectrochemical analysis technique in which a laser pulse is used to simultaneously vaporize a small sample mass and excite the resulting atoms to emit light (Cremers and Radziemski, 2013) via formation of a hot plasma on the sample surface.

The use of the laser spark and elemental analysis of a LIBS spectrum to detect biological contaminations has been published by a number of researchers. For example, Morel et al. revealed that LIBS could detect and sort species of six bacteria and two pollens (Morel et al., 2003). Rehse et al. and Diedrich et al. showed that both pathogenic and non-pathogenic *Escherichia coli* (*E. coli*) cultured strains grown in both nutrient-rich and nutrient-free media can be differentiated using a statistical analysis of LIBS spectra of these targets (Rehse et al., 2007 and Diedrich et al., 2007). There are many other publications easily found in the literature demonstrating that light emissions from a laser spark can be used to scan for biological contaminations.

The use of the laser spark and multivariate analysis of a LIBS spectrum to detect biological contaminations has also been published: Multari et al. used multivariate analysis of the entire spectrum to detect bacterial species as well as strains of *E. coli* (Multari et al., 2010); to identify and discriminate bacteria, parasites, and viruses on substrates (Multari et al., 2012); to detect the presence of pesticides and dioxins in tissue fats and rendering oils (Multari et al. 2013); to detect the presence of pathogens on foods and on food preparation surfaces (Multari et al., 2013b); as well as to discriminate bacterial pathogens and methicillin-resistant *Staphylococcus aureus* (*S. aureus*) strains grown on blood agar (Multari et al., 2013c). First proof-of-principle experiments demonstrating the use of LIBS for the differentiation of pathogens spiked into human blood and Herpes Simplex virus in cerebral spinal fluid without any growth requirement in the sample preparation using multivariate analysis methods was presented at the 21st International Conference on Biodetection Technologies (Multari et al., 2013d). Subsequent work was presented at the 25th Conference on Biodetection Technologies (Fisher, et al., 2017) and the 26th Conference on Biodetection Technologies (Fisher, et al., 2018).

There are also a number of patents and patent applications related to the use of light emission from a laser spark generated on a sample to determine if pathogens are present: United States Patent Publication No. US2011/0246145A1, to Multari et al., entitled "Methods for Forming Recognition Algorithms for Laser-induced Breakdown Spectroscopy", describes a specific method for creating a programmable detection algorithm to detect contaminations or differentiate samples using the laser spark by sequentially identifying a detection target from a group of detection targets, and then using a "drill down" approach to sequentially identify all other samples that the algorithm is designed to detect; United States Patent Publication No. US2011/0171636A1, to Melikechi et al., "Mono- and Multi-element Coded LIBS Assays and Methods", describes a method for identifying objects with unique elemental-coded markers or tags prior to LIBS analysis to enable quick identification; and United States Patent Publication No. US 2015/0284763 A1, to Rehse, "Method of Using Laser-Induced Breakdown Spectroscopy for the Identification and Classification of Bacteria" describes a method of detecting bacteria in complex samples using emissions from a laser spark to analyze for bacteria by comparing the atomic emission spectral fingerprint against a pre-compiled library of spectral fingerprints from previously identified organisms for matching the unknown spectral fingerprint and identifying the obtained spectral fingerprint using a chemometric algorithm which may optionally include multivariate and other analysis methods in combination with the use of the library. The patent by Multari et al. is limited in that it prescribes a very particular way of building a detection algorithm and is not inclusive of variations in the way the predictive models could be constructed in the development of the detection algorithm. The patent by Melikechi et al. is limited to the use of elemental-coded markers or "tags" to identify biological and chemical molecules and does not specifically discuss pathogens or chemicals composed of biological and chemical molecules in complex matrices such as blood. The application by Rehse makes use of a library as part of the detection and includes multivariate methods as optional components that can be added. This patent does not make use of statistical analysis methods in combination with chemometric modeling. It also does not discuss combined predictive modeling to create an algorithm for the detection of pathogens.

References cited herein include:

Cremers, D. A.; Radziemski, L. J. (2013) Handbook of Laser-Induced Breakdown Spectroscopy, 2nd ed., John Wiley, and Sons: Chichester, U.K.

Diedrich, J.; Rehse, S. J; Palchaudhuri, S. (2007) *Escherichia coli* identification and strain discrimination using nanosecond laser-induced breakdown spectroscopy, Appl. Phys. Lett. 90, 163901 1-3.

Fisher, C.; Multari, R.; Nelson, A.; Cremers, D. A. and Duncan, R. (2017) Multiplex Detection of Protozoan, Bacterial, and Viral Pathogens in Human Blood Using Laser-Induced Breakdown Spectroscopy, 25th International Biodetection Technologies Conference, June 26-28, Alexandria, Va. USA.

Fisher, C.; Multari, R.; Cremers, D. A.; Nelson, A.; Young, S.; Karimi, Z. and Duncan, R. (2018) Multiplex Detection of Protozoan, Bacterial, and Viral Pathogens in Human Blood Using Laser-Induced Breakdown Spectroscopy, 26th International Biodetection Technologies Conference, June 27-28, Bethesda, Md. USA.

Morel, S.; Leone, N.; Adam, P.; Amouroux, J. (2003) Detection of bacteria by time resolved laser-induced breakdown spectroscopy, Appl. Opt. 42, 6184-6191.

Multari, R. A.; Cremers, D. A.; Dupre, J. M. and Gustafson, J. E. (2010) The Use of Laser-Induced Breakdown Spectroscopy (LIBS) for Distinguishing Between Bacterial Pathogen Species and Strains, Appl. Spectrosc. 64, 750-759.

Multari, R. A.; Cremers, D. A. and Bostian, M. L. (2012) Use of laser-induced breakdown spectroscopy for the differentiation of pathogens, and viruses on substrates, Appl. Opt. 51, B57-B64.

Multari, R. A.; Cremers, D. A.; Scott, T. and Kendrick, P. (2013) Detection of Pesticides and Dioxins in Tissue Fats and Rendering Oils Using Laser-Induced Breakdown Spectroscopy (LIBS). J. Agric Food Chem. 61, 2348-2357.

Multari, R. A.; Cremers, D. A.; Dupre, J. M. and Gustafson, J. E. (2013b) The Detection of Biological Contaminants on Foods and Food Surfaces Using Laser-Induced Breakdown Spectroscopy (LIBS). J. Agric Food Chem. 61, 8687-8694.

Multari, R. A.; Cremers, D. A.; Bostian, M. L.; Dupre, J. M. and Gustafson, J. E. (2013c) Proof of Principle for a Real-Time Pathogen Isolation Media Diagnostic: The Use of Laser-Induced Breakdown Spectroscopy (LIBS) to Discriminate Bacterial Pathogens and Antimicrobial-Resistant *Staphylococcus Aureus* Strains Grown on Blood Agar, J. Pathogens 2013, Article ID 898106, 11 pages; http://dx.doi.org/10.1155/2013/898106.

Multari, R.; Cremers, D. A.; Duncan, R. and Young, S. (2013d) Laser-Induced Breakdown Spectroscopy as a Rapid, In-situ Clinical Diagnostic, 21st International Conference on Biodetection Technologies 2013 Technological Advances in Detection & Identification of Biological Threats, Alexandria, Va., USA, 18-19.

Rehse, S. J.; Diedrich, J. and Palchaudhuri, S. (2007) Pathogenic *Escherichia coli* strain discrimination using laser-induced breakdown spectroscopy, J. Appl. Phys. 102, 014702.

BRIEF SUMMARY OF THE INVENTION

The present invention is of an apparatus for rapid detection of a plurality of pathogens and/or chemicals, the apparatus comprising: a laser generating laser-induced breakdown spectra from a sample inserted into the apparatus; a receiver recording the spectra; a data analysis component acquiring the spectra from the receiver; and a display and/or data storage component displaying and/or receiving from the data analysis component which pathogens and/or chemicals are present in the sample and/or the likelihood of such presence; wherein the data analysis component comprises: predictive models for the plurality of pathogens and/or chemicals; a queue to order automated analysis by the predictive models in a predetermined order; and statistical analysis models for each of the predictive models to automatically provide likelihoods of presence of the respective pathogens and/or chemicals. In certain embodiments, the data analysis component additionally comprises one or more models identifying one or more atomic emissions in the spectra. The sample may be a liquid sample dried onto a filter, such as a blood sample, the sample preferably having no active pathogens. Preferably, each of the predictive models are generated by multivariate analysis (and preferably also statistical analysis) of laser-induced breakdown spectra of samples containing the corresponding pathogen or chemical and samples not containing the corresponding pathogen or chemical. The apparatus can additionally comprise a mirror (and also focusing lens) directing light from the laser onto the sample. The laser is preferably a pulsed laser.

The invention is further of a method for rapid detection of a plurality of pathogens and/or chemicals, the method comprising: generating laser-induced breakdown spectra from a sample; acquiring and recording the spectra; analyzing the spectra; and automatically displaying and/or storing which pathogens and/or chemicals are present in the sample and/or the likelihood of such presence; wherein analyzing comprises: employing predictive models for the plurality of pathogens and/or chemicals; employing a queue to order automated analysis by the predictive models in a predetermined order; and employing statistical analysis models for each of said predictive models to automatically provide likelihoods of presence of the respective pathogens and/or chemicals. In certain embodiments, analyzing additionally comprises one or more models identifying one or more atomic emissions in the spectra. The sample may be a liquid sample dried onto a filter, such as a blood sample, the sample preferably having no active pathogens. Preferably, each of the predictive models are generated by multivariate analysis (and preferably also statistical analysis) of laser-induced breakdown spectra of samples containing the corresponding pathogen or chemical and samples not containing the corresponding pathogen or chemical. The apparatus can additionally comprise a mirror (and also focusing lens) directing light from the laser onto the sample. The laser is preferably a pulsed laser.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention employs advanced mathematical methods based on multivariate analysis such as partial least squares discriminate analysis combined with statistical analysis to create a pathogen detection algorithm that can be used for the rapid, real-time detection of pathogens. The predictive models are combined in a logical flow to create detection programming for use on an instrument. Statistical analysis of the prediction results of the models used in the detection algorithm is included as part of the algorithm analysis flow. This invention does not use a library of previously identified organisms or chemicals as has been previously patented; does not make use of elemental markers or "tags" to identify biological or chemical molecules as has been previously patented; and does not require a "drill down" approach in the development of the detection algorithm as has been previously patented. This invention is therefore different from the previous patents related to the use of light emissions from a laser spark for the detection of biological or chemical contaminations.

Some implementations can include an instrument for the rapid analysis and detection of pathogens or chemicals in complex matrices such as blood, other bodily fluids, and water through the use of multivariate and statistical analysis methods applied to the light emissions from a laser spark on the surface of a sample to build a detection algorithm. The instrument of the invention requires only minimal sample preparation such as applying blood or other liquid directly to a filter and heat drying the sample.

The instrument has the ability to detect multiple chemicals and/or pathogens of various types (e.g., bacteria, viruses, parasites) and the ability to expand the defined set of pathogens or chemicals to be detected through additional model building and programming. The instrument needs only power to operate (batteries or wall), require simple optics, and be constructed of commercial off-the-shelf components.

This instrument can be used anywhere and does not require a laboratory to operate as the heat drying process in the sample preparation renders any active pathogens in the sample inactive. Inexpensive paper filters can be used as a substrate for analysis. The instrument is easy-to-use, does not require highly skilled operators, and analysis is preferably initiated by simply pushing a button once the sample has been inserted into the instrument. The analysis results are available within minutes once the sample has been inserted into the instrument and the time required is 10 minutes or less to apply the blood or other liquid to a filter, heat dry the sample, insert the sample into the instrument and complete the analysis of the sample. Easy to interpret analysis results are preferably displayed as text on the screen for the operator to read in addition to being stored in an electronic file.

Figure 1:
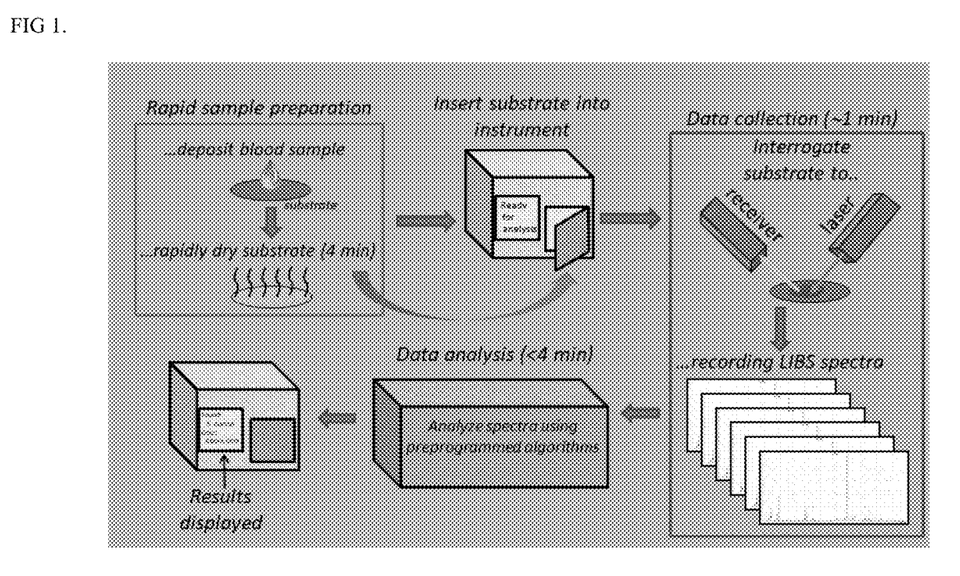
FIG. 1 is a diagram of the steps involved in the rapid analysis of blood or other liquids for the detection of pathogens or chemicals using laser-based interrogation in accordance with some implementations.

FIG. 1 is a detailed schematic of the process for detecting pathogens and/or chemicals in complex matrices such as blood, other bodily fluids, or water. The liquid sample is deposited onto a paper filter and rapidly heat dried. The filter with the dried liquid is inserted into an instrument capable of generating a laser spark on the surface of the filter. A laser inside the instrument generates laser sparks on the surface of the filter. Light emissions from the laser sparks are collected by a receiver such as a fiber optic and the spectrum from the laser spark is captured and recorded using a spectrometer.

A statistically relevant number of spectra from laser sparks generated on the surface of the sample are recorded by the spectrometer. The recorded spectra are input into a programmed algorithm for analysis to determine if specific pathogens or chemicals are present in the complex sample. The analysis results are displayed on a screen for the operator to read and recorded in a file.

Figure 2:
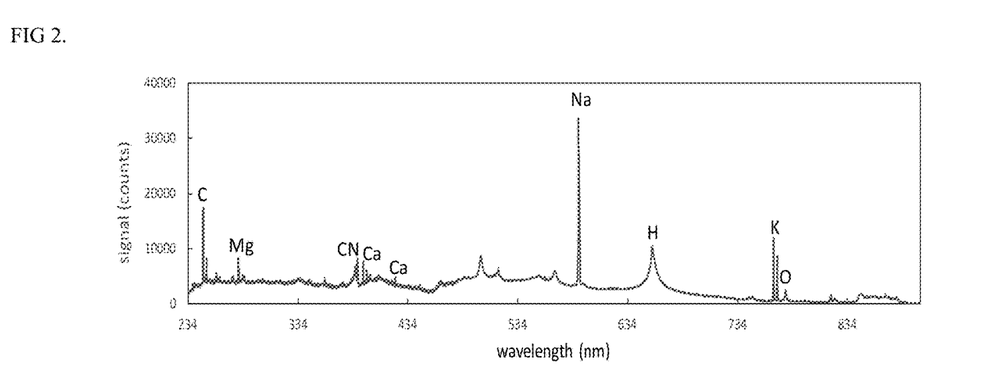
FIG. 2 is an example of a spectrum from a laser spark to which the multivariate and statistical analysis is applied in accordance with some implementations.

FIG. 2 shows an example of spectrum obtained from a laser spark on human blood. The spectrum covers a wavelength range from the ultraviolet to the infrared and the intensity of the light measured at each wavelength increment in the measured range is recorded for analysis.

Figure 3:
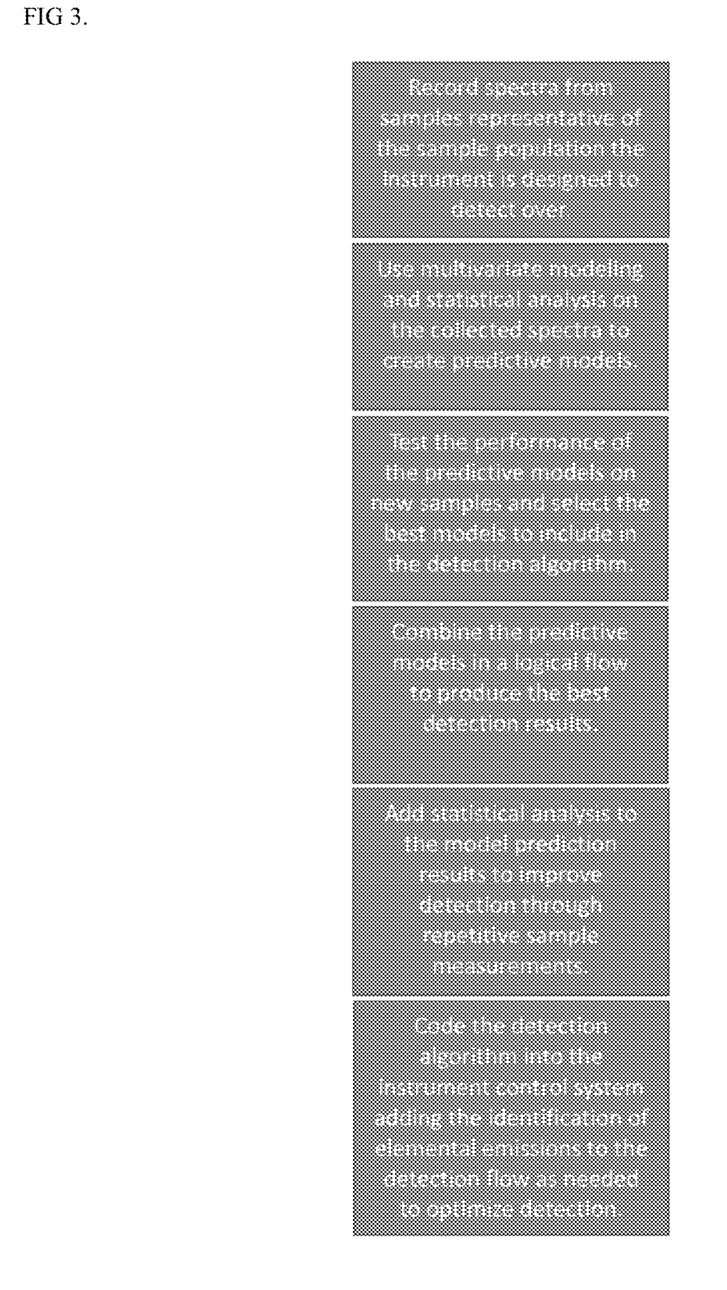
FIG. 3 is a block diagram of the method to create pathogen and/or chemical detection algorithms in accordance with some implementations.

FIG. 3 is a block diagram of the steps for developing the programmed analysis software for the detection of pathogens and/or chemicals in complex liquid matrices such as blood, other bodily fluids, or water. Spectra from samples containing the pathogens and/or chemicals to be detected and from samples without the pathogens and/or chemicals to be detected are recorded.

Multivariate analysis is applied to the recorded spectra to create predictive models to identify samples in the detection group both with and without the pathogens and/or chemicals. The predictive models are tested using spectra collected from new samples and the best performing predictive models are selected to include in the algorithm for detection.

The selected models are then arranged in a logical flow optimized to produce the best detection results. The same models may be used more than once in this flow. Statistical analysis of repetitive measurements from the same sample is added to the detection algorithm decision flow to produce the best possible detection results. Statistical methods such as averaging model prediction results and screening by the standard deviation of the modeling predictions are added to the detection decision flow.

If needed to separate different liquids or substrate materials, the identification of selected atomic emissions may be added to the detection decision flow to optimize results. That is, selected atomic emissions can also be used to identify different pathogens or chemicals when added to the detection decision flow. Once optimized, the detection flow is added to the instrument control system for the programmed analysis of unknown samples for the presence of the pathogens and/or chemicals the instrument is designed to detect.

Figure 4:
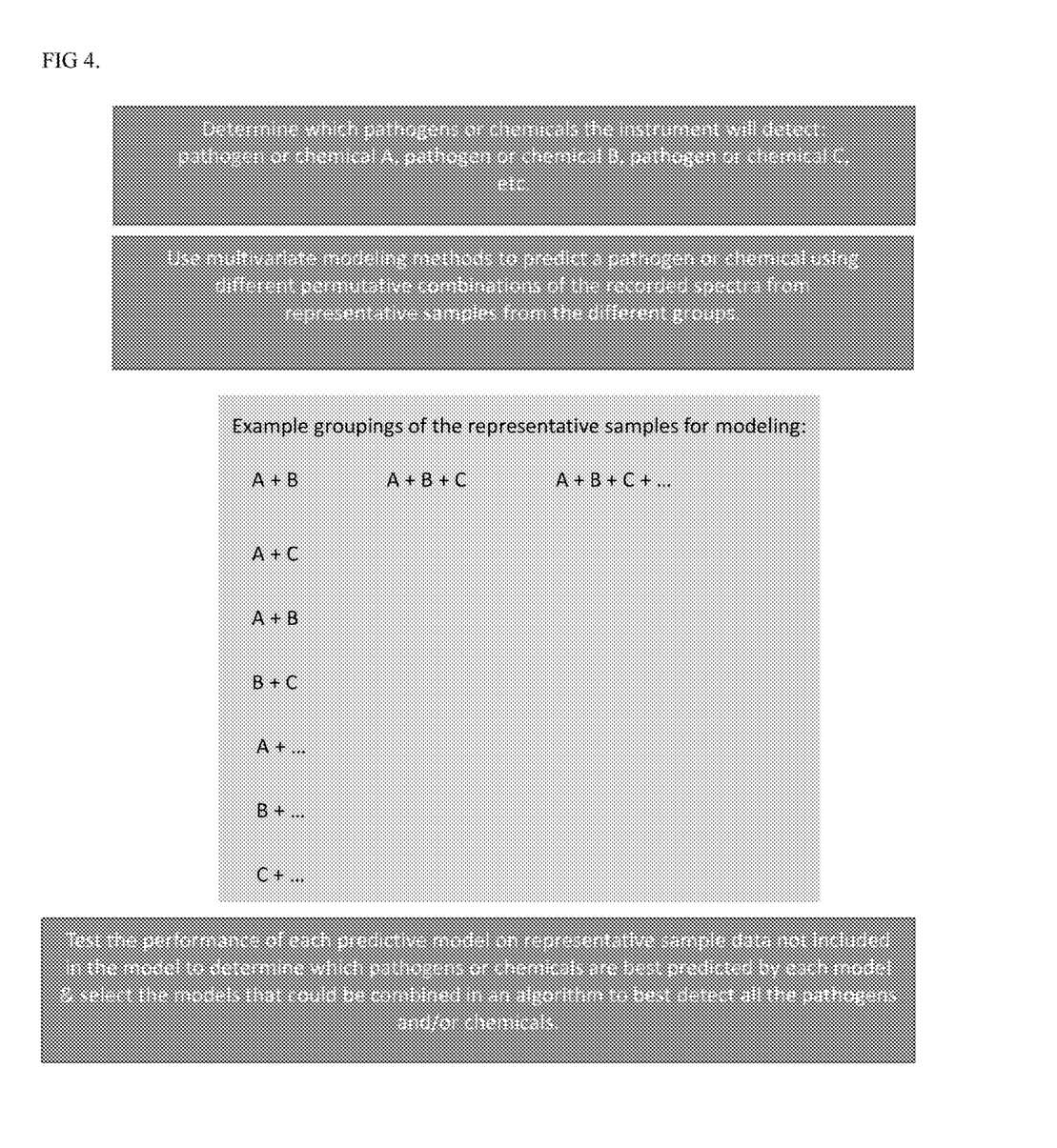
FIG. 4 is a block diagram of the method to create predictive models to be used in pathogen or chemical detection algorithms of FIG. 3 in accordance with some implementations.

FIG. 4 is a diagram representing the process for creating predictive multivariate models to be used in the development of the detection algorithm. The pathogens and/or chemicals to be included in the detection along with the relevant complex matrices without the pathogens and/or chemicals to be included in the detection are defined. Predictive models are created using different combinations of the pathogens and/or chemicals. All possible combinations and permutations of the detection targets are investigated including predictive modeling that include only a subset of the detection targets.

Predictive models generated are evaluated for performance over all the detection targets. The screening potential of each predictive model for the pathogens and/or chemicals to be detected is assessed. A set of models to be used to build the detection algorithm is selected.

Figure 5:
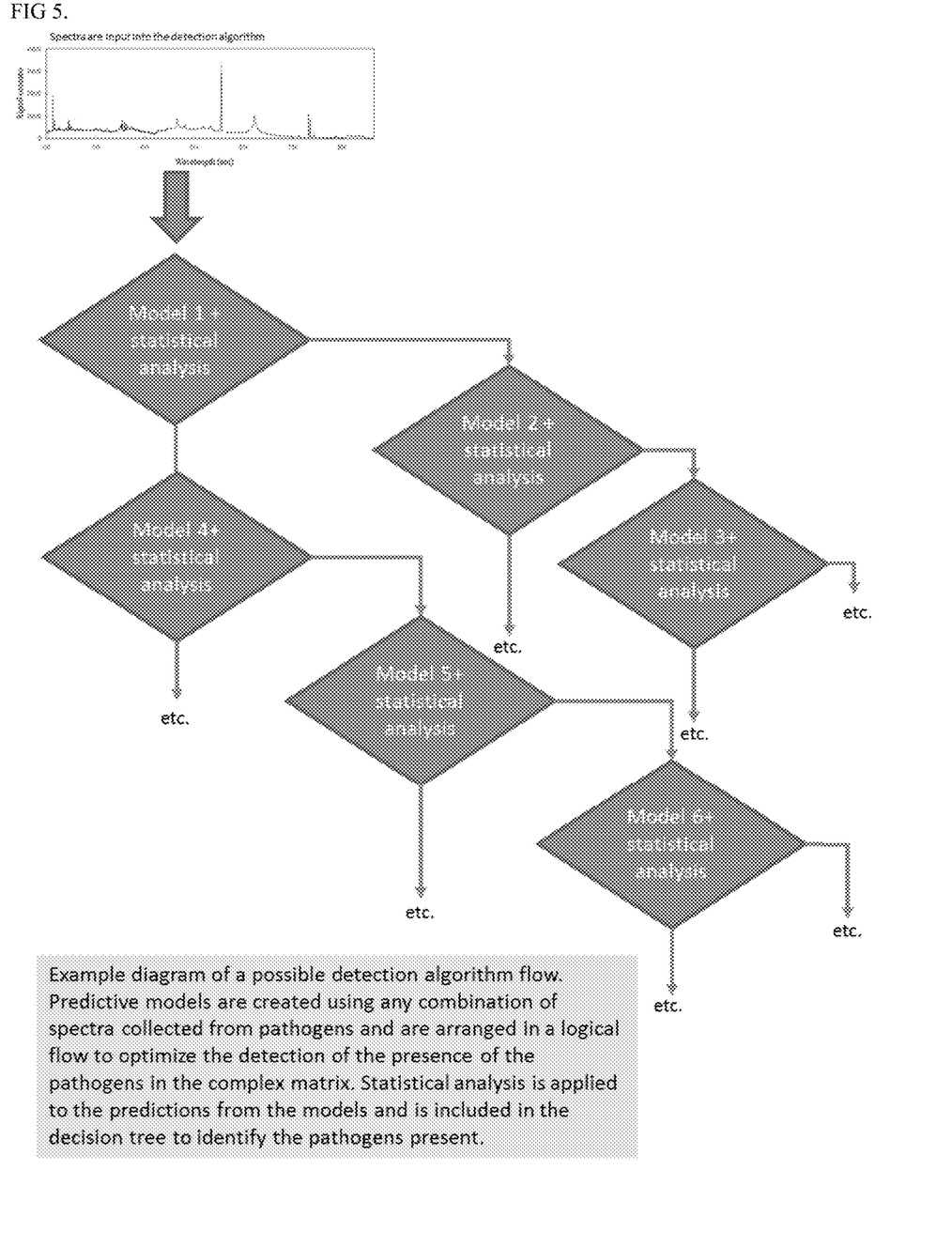
FIG. 5 is a diagram of an example of how predictive models could be combined with statistical analysis to create a detection algorithm that could be programmed into an instrument to detect pathogens or chemicals in complex matrices.

FIG. 5 shows one possible way of creating an algorithm to detect pathogens in a complex sample using the predictive models that could be programmed into an instrument. Predictive models are created using any combination of spectra collected from pathogens and are arranged in a logical flow to optimize the detection of the presence of the pathogens in the complex matrix. Statistical analysis (not shown in the diagram) is applied to the predictions from the models and is included in the decision tree to identify the pathogens present.

Figure 6:
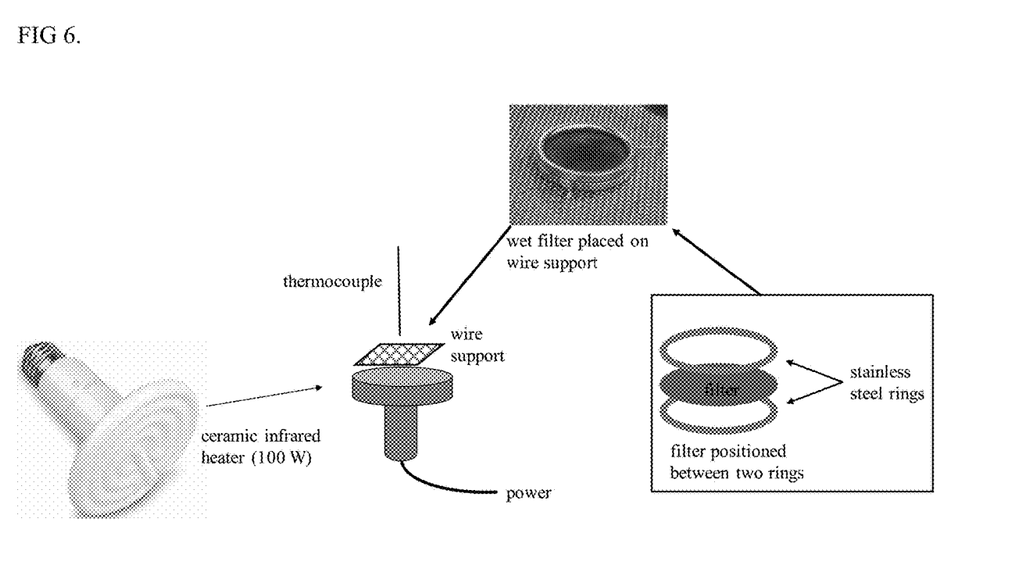
FIG. 6 is a diagram of the portion of an instrument that could be used to rapidly heat dry and deactivate any pathogens in a sample to prepare it for analysis in accordance with some implementations. In this drawing, blood is the medium in which the pathogen or chemical is to be detected.

FIG. 6 illustrates a possible method for rapidly heat drying and deactivating a liquid sample containing pathogen and/or chemical and experimental results validating that pathogens are deactivated in the drying process. A wet filter is clamped between two stainless steel rings and placed on a wire support to which a thermocouple is attached to measure temperature. A 100 W ceramic infrared heater is used to rapidly heat and dry the liquid sample. The filter is heated to above 80° C. and held at this temperature for approximately 4 minutes to deactivate the pathogens.

Figure 7:
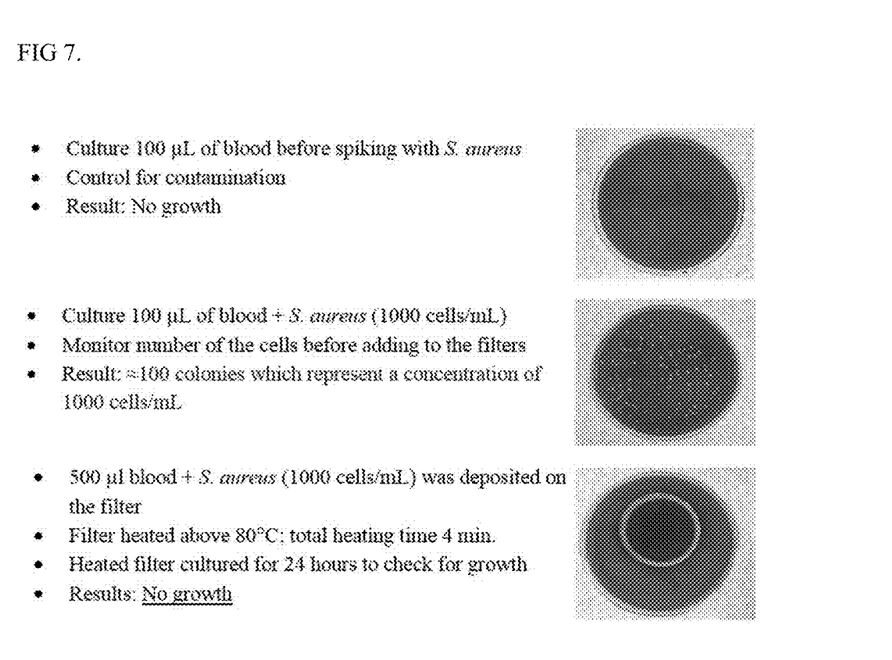
FIG. 7 shows the results of a test series to evaluate the ability to dry blood or other liquid on a filter and simultaneously deactivate a pathogen using rapid heating in accordance with some implementations.

FIG. 7 shows experimental results demonstrating that rapidly applied heat can be used to deactivate pathogens present in a sample. A filter heated to 80° C. and held at this temperature for 4 minutes does not contain active pathogens as verified by the lack of pathogen colony growth on a culture plate 24 hours later.

FIG. 8 shows the results of a detection algorithm developed as described above for the detection of blood samples containing S. aureus, HIV samples, and a mix of S. aureus and HIV when new blood samples not included in the modeling were input into the detection algorithm to test the algorithm performance. This algorithm consists of three predictive models.

Figure 8A:
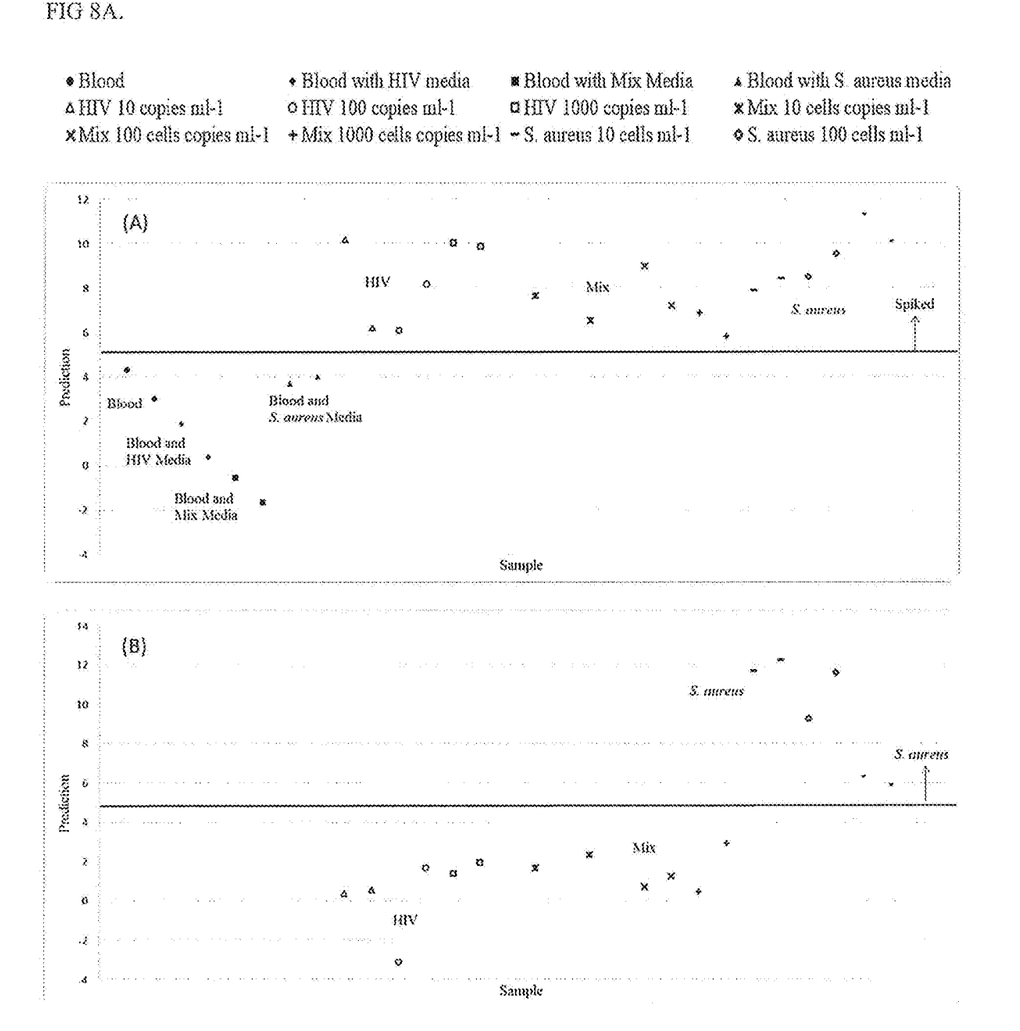
FIG. 8 shows test sample results from predictive models arranged to create an algorithm in accordance with some implementations (note that ml-1 in the legend should be read as $ml^{-1}$).

FIG. 8 (A) shows test sample results from the first predictive model in an algorithm created to separate S. aureus, HIV samples, and a mix of S. aureus and HIV. This model was created without any mixed sample data but correctly identifies the mixed samples as pathogen spiked samples.

Figure 8B:
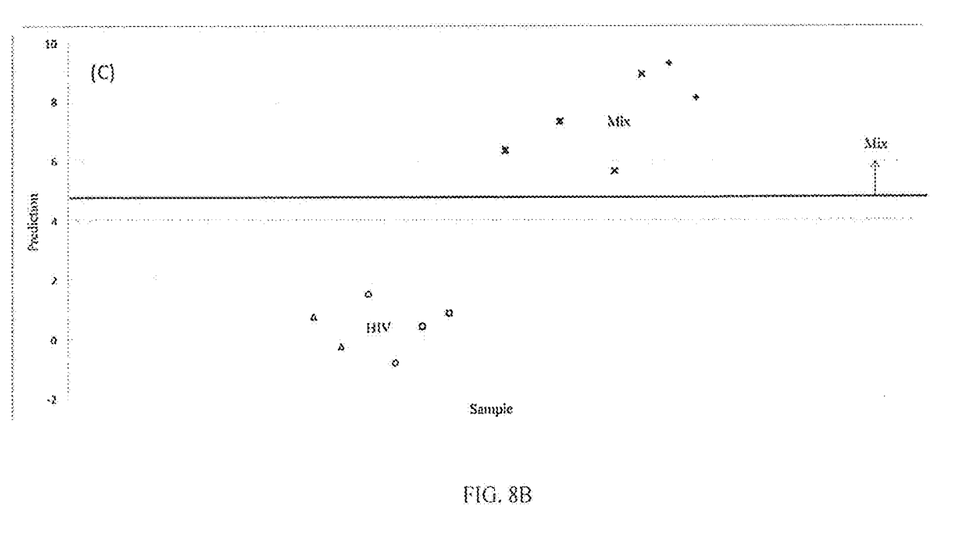

FIG. 8 (B) shows test sample results from the second predictive model in an algorithm created to separate S. aureus, HIV samples, and a mix of S. aureus and HIV. This model was created to separate S. aureus from HIV and mixed samples and had no mixed samples in the modeling.

FIG. 8 (C) shows test sample results from the third predictive model in an algorithm created to separate S. aureus, HIV samples, and a mix of S. aureus and HIV. This model was created to separate mixed samples from HIV samples.

Figure 9:
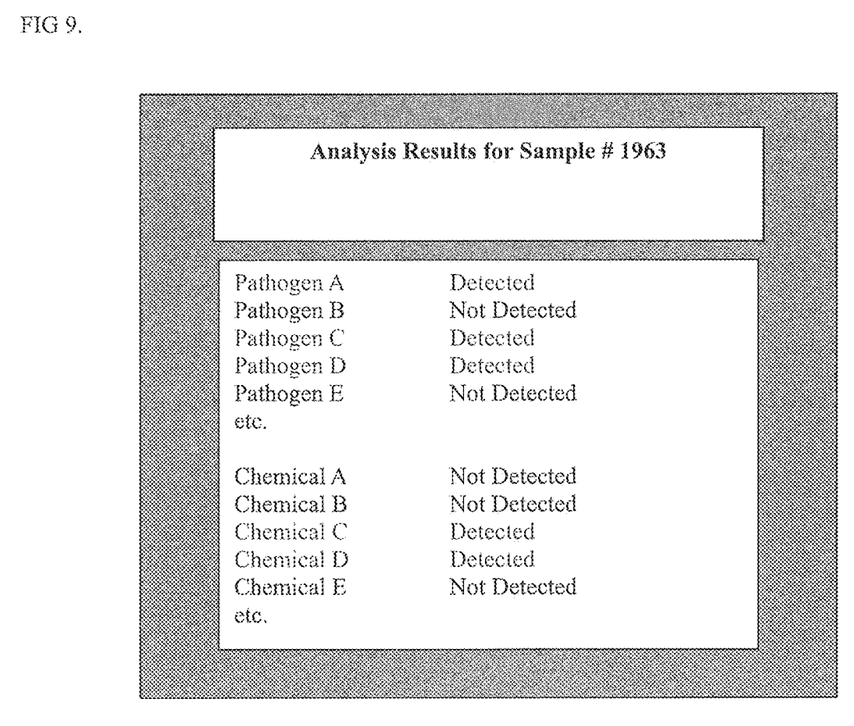
FIG. 9. is a conceptual drawing of user interface that will report analysis results to the instrument operator in a simple, easy to read and interpretive manner in accordance with some implementations.

FIG. 9 shows an example of a possible simple text output that could be displayed to the instrument operator indicating analysis results. The sample ID number is shown and each pathogen or chemical tested for is displayed along with a simple statement on whether or not the pathogen or chemical was detected.

Figure 10:
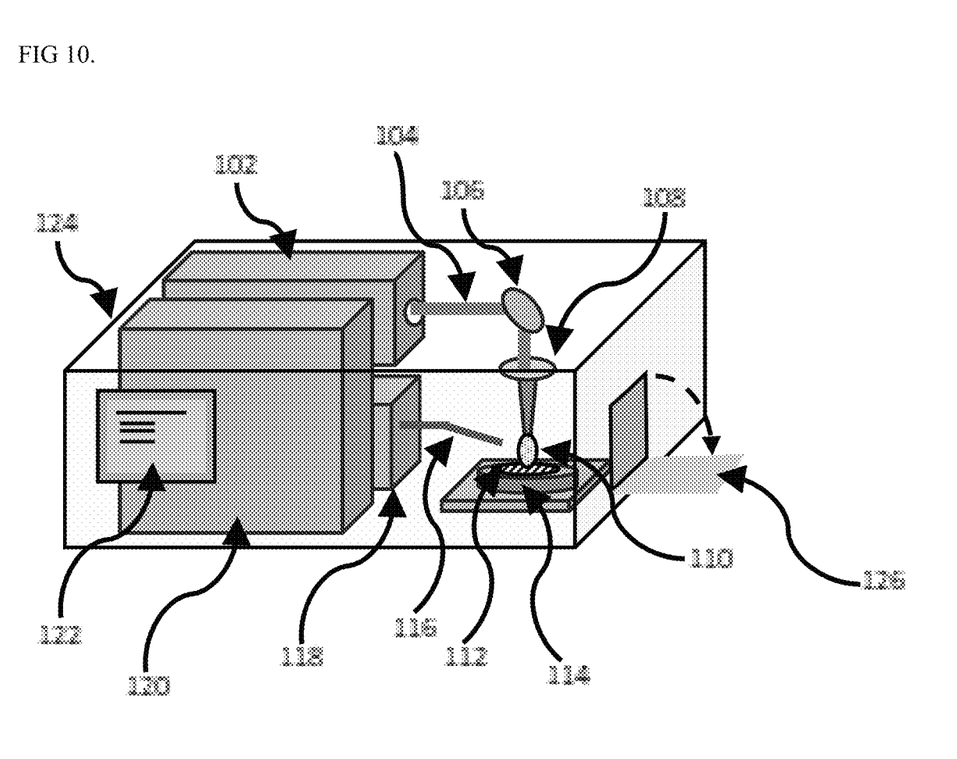
FIG. 10 is a conceptual drawing of a wall or battery-powered instrument that can be used in any environment.

FIG. 10 diagrams a possible design for an instrument to generate laser sparks on the surface of a sample, record the spectra from the light emissions of the laser sparks, process the recorded spectra through a detection algorithm, and simply display the analysis results to the instrument operator.

The following reference numerals identify elements of the Figures:
- 102 is a pulsed laser.
- 104 is the laser beam emitted from the laser.
- 106 is a mirror used to turn the laser beam onto the sample.
- 108 is a focusing lens to generate the laser spark on the surface of the sample.
- 110 is the laser spark generated on the surface of the sample.
- 112 is the sample applied to a substrate.
- 114 is a translation stage that moves the sample such that each laser spark interrogates a fresh spot on the sample.
- 116 is a fiber optic that collects the light emitted from the laser spark on the sample.
- 118 is a spectrometer that resolves and records the spectrum from each laser spark generated on the sample.
- 120 is a computer used to control the operation of the laser, the translation stage, and the spectrometer and to analyze the recorded spectra using the detection algorithm.
- 122 is a screen on which the detection results are displayed to the instrument operator.
- 124 is the instrument housing.
- 126 is a door through which a sample can be placed in the instrument for analysis.

It is, therefore, apparent that there is provided, in accordance with the various embodiments disclosed herein, a method of detecting pathogens and chemicals in complex matrices, and a concomitant apparatus. Embodiments of the method of the invention can include one or more of the following benefits:

A pathogen and/or chemical detection method that operates solely on electrical power (wall or battery).

A pathogen and/or chemical detection method that does not require any pre-concentration of a sample.

A pathogen and/or chemical preparation method that rapidly heat dries and deactivates any pathogens in a sample so that it is dry and safe for analysis in any environment.

A pathogen and/or chemical detection method that uses spectroscopic signals from a laser-generated spark for analysis but does not rely solely on the identification of specific elemental emissions or a spectral library for analysis.

A pathogen and/or chemical detection method that accomplishes detection through multivariate analysis of signal collected from a sample to create predictive models that can be arranged creatively to accurately and repeatedly predict the identify of a pathogen in a sample.

A pathogen and/or chemical detection method that uses multiple redundant models created by grouping samples in different ways to improve detection accuracy.

A pathogen and/or chemical detection method that improves accuracy through the use of repetitive sampling and statistical analysis of sample prediction results.

A pathogen and/or chemical detection method that screens for a defined set of pathogens using predictive models created with all or just a subset of the pathogens or chemicals included in the pathogen and/or chemical set to be detected.

A pathogen and/or chemical detection method that can identify pathogen or chemical samples that are not part of the pathogen or chemical detection target group as "unknown" through the use of statistical parameters associated with the predictive modeling.

A pathogen and/or chemical detection method that delivers results rapidly.

A pathogen and/or chemical detection method that reports results simply and can be used without requiring advanced technical training.

Experimental evidence of the utility, novelty, and non-obviousness of the present invention is provided in R. A. Multari, et al., "The use of laser-based diagnostics for the rapid identification of infectious agents in human blood," J. of Applied Microbiology 126, 1606-1617 (2019), which is incorporated by reference herein.

Embodiments of the present invention provide a technology-based solution that overcomes existing problems with the current state of the art in a technical way to satisfy an existing problem for identifying multiple pathogens or chemicals. An embodiment of the present invention is necessarily rooted in computer technology in order to overcome a problem specifically arising in the realm of signal processing. Embodiments of the present invention achieve important benefits over the current state of the art, such as increased flexibility, faster detection times, smaller memory requirements, and like benefits. Certain of the unconventional steps of embodiments of the present invention include employment of predictive models for a plurality of pathogens and/or chemicals, a queue to order automated analysis by the predictive models in a predetermined order, and statistical analysis models for each of the predictive models to automatically provide likelihoods of presence of the respective pathogens and/or chemicals.

In the preferred embodiment, and as readily understood by one of ordinary skill in the art, the apparatus according to the invention will include a general or specific purpose computer or distributed system programmed with computer software implementing the steps described above, which computer software may be in any appropriate computer language, including C++, FORTRAN, BASIC, Java, assembly language, microcode, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements.

Note that in the specification and claims, "about" or "approximately" means within ten percent (10%) of the numerical amount cited. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. An apparatus for rapid detection of a plurality of pathogens and/or chemicals, said apparatus comprising:
   a laser generating laser-induced breakdown spectra from a sample inserted into said apparatus;
   a receiver recording the spectra;

a data analysis component acquiring the spectra from said receiver without reference to other types of spectra; and a display and/or data storage component displaying and/or receiving from said data analysis component which pathogens and/or chemicals are present in the sample and/or the likelihood of such presence;

wherein said data analysis component comprises:

predictive models for the plurality of pathogens and/or chemicals;

a queue to order automated analysis by said predictive models in a predetermined order; and statistical analysis models for each of said predictive models to automatically provide likelihoods of presence of the respective pathogens and/or chemicals using multivariate analysis methods applied to all or one or more selected regions of the spectra.

2. The apparatus of claim 1 wherein said data analysis component additionally comprises one or more models identifying a sample using all of or one or more selected regions in the spectra to make a mathematical data set to which multivariate analysis methods are applied to create predictive models to use for identification.

3. The apparatus of claim 1 wherein the sample is a liquid sample dried onto a filter.

4. The apparatus of claim 3 wherein the sample is a blood sample.

5. The apparatus of claim 1 wherein each of said predictive models are generated by mathematical predictive methods applied to all or one or more selected regions of the laser-induced breakdown spectra of samples containing the corresponding pathogen or chemical and samples not containing the corresponding pathogen or chemical.

6. The apparatus of claim 5 wherein each of said predictive models are generated by multivariate analysis and statistical analysis applied to all or selected regions of laser-induced breakdown spectra of samples containing the corresponding pathogen or chemical and samples not containing the corresponding pathogen or chemical.

7. The apparatus of claim 1 wherein said apparatus additionally comprises a mirror directing light from the laser onto the sample.

8. The apparatus of claim 7 wherein said apparatus additionally comprises a focusing lens between said mirror and the sample.

9. The apparatus of claim 1 wherein said laser is a pulsed laser.

10. A method for rapid detection of a plurality of pathogens and/or chemicals, the method comprising the steps of:

generating laser-induced breakdown spectra from a sample;

acquiring and recording the spectra;

analyzing the spectra without reference to other types of spectra; and automatically displaying and/or storing which pathogens and/or chemicals are present in the sample and/or the likelihood of such presence;

wherein analyzing comprises:

employing predictive models for the plurality of pathogens and/or chemicals;

employing a queue to order automated analysis by the predictive models in a predetermined order; and employing statistical analysis models for each of said predictive models to automatically provide likelihoods of presence of the respective pathogens and/or chemicals analyzing using methods applied to all or one or more selected regions of the spectra.

11. The method of claim 10 wherein analyzing additionally comprises one or more models identifying a sample using one or more regions of the spectra to make a mathematical data set to which multivariate analysis methods are applied to create predictive models that can be used to identify the sample.

12. The method of claim 10 wherein the sample is a liquid sample dried onto a filter.

13. The method of claim 12 wherein the sample is a blood sample.

14. The method of claim 10 wherein each of the predictive models are generated by multivariate analysis of laser-induced breakdown spectra of samples containing the corresponding pathogen or chemical and samples not containing the corresponding pathogen or chemical using multivariate analysis methods applied to all or one or more regions of the spectra.

15. The method of claim 14 wherein each of the predictive models are generated by multivariate analysis and statistical analysis of laser-induced breakdown spectra of samples containing the corresponding pathogen or chemical and samples not containing the corresponding pathogen or chemical using multivariate analysis methods applied to all or one or more selected regions of the spectra.

16. The method of claim 10 additionally comprising employing a mirror to direct light from a laser onto the sample.

17. The method of claim 16 additionally comprising employing a focusing lens between the mirror and the sample.

18. The method of claim 16 wherein the laser is a pulsed laser.

* * * * *